(12) United States Patent
Bronkalla et al.

(10) Patent No.: US 10,083,504 B2
(45) Date of Patent: Sep. 25, 2018

(54) MULTI-STEP VESSEL SEGMENTATION AND ANALYSIS

(71) Applicant: INTERNATIONAL BUSINESS MACHINES CORPORATION, Armonk, NY (US)

(72) Inventors: Mark Bronkalla, Hartland, WI (US); Colin Compas, San Jose, CA (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 37 days.

(21) Appl. No.: 15/258,837

(22) Filed: Sep. 7, 2016

(65) Prior Publication Data

US 2018/0068437 A1   Mar. 8, 2018

(51) Int. Cl.
| | |
|---|---|
| *G06K 9/00* | (2006.01) |
| *G06T 7/00* | (2017.01) |
| *G06K 9/62* | (2006.01) |
| *G06K 9/46* | (2006.01) |
| *G06T 7/60* | (2017.01) |
| *G06K 9/52* | (2006.01) |
| *G06K 9/66* | (2006.01) |
| *A61B 5/00* | (2006.01) |
| *A61B 5/02* | (2006.01) |

(52) U.S. Cl.
CPC ........ *G06T 7/0012* (2013.01); *A61B 5/02007* (2013.01); *A61B 5/7264* (2013.01); *A61B 5/742* (2013.01); *G06K 9/4604* (2013.01); *G06K 9/52* (2013.01); *G06K 9/6267* (2013.01); *G06K 9/66* (2013.01); *G06T 7/0085* (2013.01); *G06T 7/60* (2013.01); *G06T 2207/30101* (2013.01)

(58) Field of Classification Search
CPC ................ G06T 7/0012; G06T 7/0083; G06T 2207/30004; G06T 7/0081; G06T 2207/10116; G06T 5/40; G06T 2207/30068; G06F 19/321
See application file for complete search history.

(56) References Cited

U.S. PATENT DOCUMENTS

| | | |
|---|---|---|
| 6,047,080 A | 4/2000 | Chen et al. |
| 7,620,225 B2 | 11/2009 | Rinck et al. |
| 7,711,165 B2 | 5/2010 | Lesage et al. |
| 2005/0110791 A1 | 5/2005 | Krishnamoorthy et al. |
| 2016/0196660 A1 | 7/2016 | Prevrhal et al. |

FOREIGN PATENT DOCUMENTS

WO   WO2010041201 A1   4/2010

OTHER PUBLICATIONS

Kirbas et al., "A Review of Vessel Extraction Techniques and Algorithms", http://www.siue.edu/, 2003.

*Primary Examiner* — Duy M Dang
(74) *Attorney, Agent, or Firm* — Erik Huestis; Stephen Kenny; Foley Hoag LLP

(57) ABSTRACT

Multi-step vessel segmentation and analysis is provided. In various embodiments, a branch detection algorithm is applied to a medical image to determine a plurality of branches of a blood vessel appearing in the medical image. A plurality of segments of the blood vessel appearing in the medical image is determined. Each of the plurality of segments is bounded by one of the plurality of branches. An edge detection algorithm is applied piecewise to each of the plurality of segments. A composite blood vessel outline is formed from the piecewise edge detection.

20 Claims, 4 Drawing Sheets

MULTI-STEP VESSEL SEGMENTATION AND ANALYSIS

BACKGROUND

Embodiments of the present invention relate to vessel segmentation, and more specifically, to multi-step vessel segmentation and analysis.

BRIEF SUMMARY

According to embodiments of the present disclosure, methods of and computer program products for vessel segmentation are provided. A branch detection algorithm is applied to a medical image to determine a plurality of branches of a blood vessel appearing in the medical image. A plurality of segments of the blood vessel appearing in the medical image is determined. Each of the plurality of segments is bounded by one of the plurality of branches. An edge detection algorithm is applied piecewise to each of the plurality of segments. A composite blood vessel outline is formed from the piecewise edge detection.

DETAILED DESCRIPTION

Figure 1:
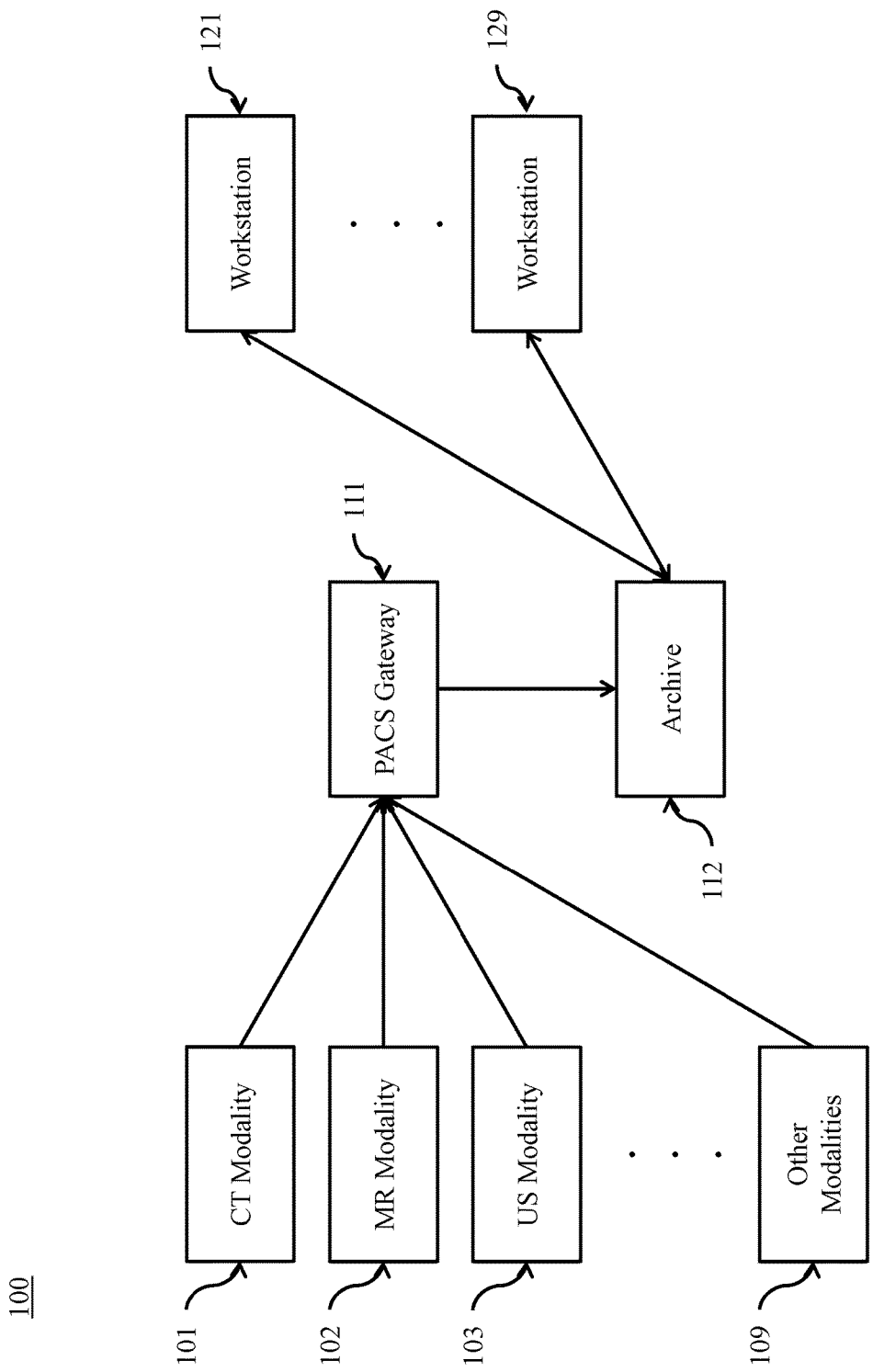
FIG. 1 depicts an exemplary Picture Archiving and Communication System.

A Picture Archiving and Communication System (PACS) is a medical imaging system that provides storage and access to images from multiple modalities. In many healthcare environments, electronic images and reports are transmitted digitally via PACS, thus eliminating the need to manually file, retrieve, or transport film jackets. A standard format for PACS image storage and transfer is DICOM (Digital Imaging and Communications in Medicine). Non-image data, such as scanned documents, may be incorporated using various standard formats such as PDF (Portable Document Format) encapsulated in DICOM.

In many cases, the coronary arteries are imaged via x-ray cine (XA) techniques in the cardiac catheterization lab or Computed Tomography angiography (CCTA). In the cardiac catheterization lab, the procedure is performed by the cardiologist to capture images of the coronary arteries and then judge them to make a decision to then perform an intervention such as a balloon angioplasty or implant a stent. This is based on visualizing the degree of narrowing of stenosis. This may also be measured by manual means or automated quantification programs. There are treatment guidelines that require the stenosis value be measured prior to intervention and the values must be reported both within the hemodynamic monitoring system and in the physicians procedure report. When implanting a stent not only is the degree of stenosis needed for justification of the need for the procedure but also the absolute diameter of the vessel lumen is required to choose the correct size stent.

When performing the catheterization procedure multiple successive views of a vessel may be captured from a variety of angles to better visualize the vessels. These images are captured in quick succession to minimize stress on the patient.

Cognitive computing provide new potentials for automatically segmenting or outlining the blood vessels whether for coronary arteries or other portions of the vasculature. Once a vessel has been segmented it can be registered with and compared to an anatomical atlas to automatically provide the vessel and segment names. However, the techniques that provide the vessel segmentation may not provide the necessary degree of accuracy required for high grade cases (e.g., ≥80% stenosis) or the precision required of the vessel lumen diameter required for stenting. Various software approaches may provide the needed degree of accuracy. However, such approaches generally must be guided to measure a selected vessel segment of interest by the user.

An additional problem is the correct automatic calculation of the vessel centerline. One means of providing automated diameter and cross sectional measurements of the vessel lumen is to calculate the centerline of the vessel and then make the measurements perpendicular to the centerline. The centerline, however, can be kinked or otherwise inaccurate in the case of extremely tortuous vessels or when dealing with a highly eccentric lesion. Eccentric lesions are those that are not a mere uniform narrowing of the vessel but rather where the plaque causing the narrowing is largely placed on one side of the vessel. If the centerline is kinked, the diameter and area measurements will be overstated, leading to inaccurate measurements and inaccurate percent stenosis calculations. Cognitive computing vessel segmentation can provide a better centerline by several methods, one of which is an averaging of the image outlines from multiple frames of the acquisition.

According to various embodiments of the present disclosure, cognitive computing vessel segmentation is applied to identify the vessels and the lesions and then automatically select the region around the lesion to perform the stenosis measurement. In some embodiments, links are provided form the measurements to the underlying images in an automated manner. Exemplary algorithms suitable for use according to embodiments of the present disclosure are described in U.S. Pat. Nos. 9,064,306 and 9,053,551 and in U.S. Pub. Nos. 2015/0126860 and 2015/0282777, each of which is hereby incorporated by reference.

In various embodiments, the cognitive computing vessel segmentation is performed by a neural network. Suitable artificial neural networks include but are not limited to a feedforward neural network, a radial basis function network, a self-organizing map, learning vector quantization, a recurrent neural network, a Hopfield network, a Boltzmann machine, an echo state network, long short term memory, a bi-directional recurrent neural network, a hierarchical recurrent neural network, a stochastic neural network, a modular neural network, an associative neural network, a deep neural network, a deep belief network, a convolutional neural networks, a convolutional deep belief network, a large memory storage and retrieval neural network, a deep Boltzmann machine, a deep stacking network, a tensor deep stacking network, a spike and slab restricted Boltzmann machine, a compound hierarchical-deep model, a deep coding network, a multilayer kernel machine, or a deep Q-network.

Cognitive computing generally requires ground truth marking of the anatomy. To manually do this with the precision required is time consuming. To iteratively apply the automated measurement technique as above and then build a precision composite vessel outline greatly speeds up the training of the cognitive computing system. Using automated vessel quantification offers higher accuracy and repeatability than manual tracing or measurement.

According to various embodiments of the present disclosure, an automated process for vessel segmentation and recognition of the stenotic segments is provided. Precision measurement is triggered for each of the identified stenosis. The stenosis characteristics, such as normal vessel diameter near the stenosis, minimum diameter and the associated areas, and percent stenosis, are displayed for each lesion.

According to various embodiments of the present disclosure, improved centerline and stenosis vessel measurements are provided. In some embodiments, these measurements are made by combining the use of the centerline calculated form the segmentation and enhanced via the precision edge detection and averaged over multiple images (frames) within the acquisition. The improved centerline may then be used to derive the perpendicular measurements for the vessel diameter, area, and calculation of the percentage stenosis.

According to various embodiments of the present disclosure, the segmented vessel is registered to the atlas and the measurements obtained by the automated measurement process are placed in the correct anatomical segments (e.g., 50% stenosis of the proximal right coronary artery). This information can then be exported for inclusion in the procedure log of the hemodynamic system and the physician report as well as for submission to the cardiac registries. The textual or tabular output as well as the annotated vessel diagram (coronary tree or peripheral vascular diagram) may be exported to the reporting system. Additionally, links may be provided to the images or key objects that are representative of the segmented vessels and the stenotic segments. These are provided for inclusion in the report and graphical navigation of the study. For example, this enables a click on the coronary tree segment to take a user to the image.

According to various embodiments of the present disclosure, automated vessel segmentation builds the initial vascular model and then applies the precision quantitative measurement tools to automatically build a detailed vessel outline. The individual segmented measurements are concatenated and blended into a continuous or near continuous vessel border. This may then be used as feedback to the system for ongoing cognitive computing, minimizing or eliminating the need for manual outlining of the vessels after the initial vessel segmentation is functional.

In this way, once an initial segmentation is determined by application of a branch detection process, the individual segments may be analyzed in a piecewise fashion. In particular, while branch detection creates the segments, edge detection is applied for each segment individually. This leads to a higher precision result, and ultimately to a more precise composite vessel outline once the various piecewise edge detections are assembled.

According to various embodiments of the present disclosure, automatic segmentation and stenosis measurement and display is performed after each vessel is imaged. This speeds up the cardiac catheterization procedure and reduces the time between the diagnostic and interventional portion of the exam.

Referring to FIG. 1, an exemplary PACS 100 consists of four major components. Various imaging modalities 101 . . . 109 such as computed tomography (CT) 101, magnetic resonance imaging (MRI) 102, or ultrasound (US) 103 provide imagery to the system. In some implementations, imagery is transmitted to a PACS Gateway 111, before being stored in archive 112. Archive 112 provides for the storage and retrieval of images and reports. Workstations 121 . . . 129 provide for interpreting and reviewing images in archive 112. In some embodiments, a secured network is used for the transmission of patient information between the components of the system. In some embodiments, workstations 121 . . . 129 may be web-based viewers. PACS delivers timely and efficient access to images, interpretations, and related data, eliminating the drawbacks of traditional film-based image retrieval, distribution, and display.

A PACS may handle images from various medical imaging instruments, such as X-ray plain film (PF), ultrasound (US), magnetic resonance (MR), Nuclear Medicine imaging, positron emission tomography (PET), computed tomography (CT), endoscopy (ES), mammograms (MG), digital radiography (DR), computed radiography (CR), Histopathology, or ophthalmology. However, a PACS is not limited to a predetermined list of images, and supports clinical areas beyond conventional sources of imaging such as radiology, cardiology, oncology, or gastroenterology.

Different users may have a different view into the overall PACS system. For example, while a radiologist may typically access a viewing station, a technologist may typically access a QA workstation.

In some implementations, the PACS Gateway 111 comprises a quality assurance (QA) workstation. The QA workstation provides a checkpoint to make sure patient demographics are correct as well as other important attributes of a study. If the study information is correct the images are passed to the archive 112 for storage. The central storage device, archive 112, stores images and in some implementations, reports, measurements and other information that resides with the images.

Once images are stored to archive 112, they may be accessed from reading workstations 121 . . . 129. The reading workstation is where a radiologist reviews the patient's study and formulates their diagnosis. In some implementations, a reporting package is tied to the reading workstation to assist the radiologist with dictating a final report. A variety of reporting systems may be integrated with the PACS, including those that rely upon traditional dictation. In some implementations, CD or DVD authoring software is included in workstations 121 . . . 129 to burn patient studies for distribution to patients or referring physicians.

In some implementations, a PACS includes web-based interfaces for workstations 121 . . . 129. Such web interfaces may be accessed via the internet or a Wide Area Network (WAN). In some implementations, connection security is provided by a VPN (Virtual Private Network) or SSL (Secure Sockets Layer). The clients side software may comprise ActiveX, JavaScript, or a Java Applet. PACS clients may also be full applications which utilize the full resources of the computer they are executing on outside of the web environment.

Communication within PACS is generally provided via Digital Imaging and Communications in Medicine (DICOM). DICOM provides a standard for handling, storing, printing, and transmitting information in medical imaging. It includes a file format definition and a network communications protocol. The communication protocol is an application protocol that uses TCP/IP to communicate between systems. DICOM files can be exchanged between two entities that are capable of receiving image and patient data in DICOM format.

DICOM groups information into data sets. For example, a file containing a particular image, generally contains a patient ID within the file, so that the image can never be separated from this information by mistake. A DICOM data object consists of a number of attributes, including items such as name and patient ID, as well as a special attribute containing the image pixel data. Thus, the main object has no header as such, but instead comprises a list of attributes, including the pixel data. A DICOM object containing pixel data may correspond to a single image, or may contain multiple frames, allowing storage of cine loops or other multi-frame data. DICOM supports three- or four-dimensional data encapsulated in a single DICOM object. Pixel data may be compressed using a variety of standards, including JPEG, Lossless JPEG, JPEG 2000, and Run-length encoding (RLE). LZW (zip) compression may be used for the whole data set or just the pixel data.

Figure 2:
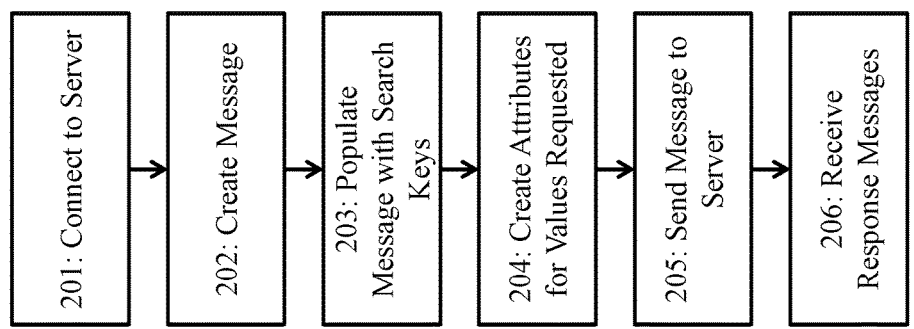
FIG. 2 illustrates an exemplary clinical image search and retrieval method.

Referring to FIG. 2, an exemplary PACS image search and retrieval method 200 is depicted. Communication with a PACS server, such as archive 112, is done through DICOM messages that that contain attributes tailored to each request. At 201, a client, such as workstation 121, establishes a network connection to a PACS server. At 202, the client prepares a DICOM message, which may be a C-FIND, C-MOVE, C-GET, or C-STORE request. At 203, the client fills in the DICOM message with the keys that should be matched. For example, to search by patient ID, a patient ID attribute is included. At 204, the client creates empty attributes for all the values that are being requested from the server. For example, if the client is requesting an image ID suitable for future retrieval of an image, it include an empty attribute for an image ID in the message. At 205, the client send the message to the server. At 206, the server sends back to the client a list of one or more response messages, each of which includes a list of DICOM attributes, populated with values for each match.

An electronic health record (EHR), or electronic medical record (EMR), may refer to the systematized collection of patient and population electronically-stored health information in a digital format. These records can be shared across different health care settings and may extend beyond the information available in a PACS discussed above. Records may be shared through network-connected, enterprise-wide information systems or other information networks and exchanges. EHRs may include a range of data, including demographics, medical history, medication and allergies, immunization status, laboratory test results, radiology images, vital signs, personal statistics like age and weight, and billing information.

EHR systems may be designed to store data and capture the state of a patient across time. In this way, the need to track down a patient's previous paper medical records is eliminated. In addition, an EHR system may assist in ensuring that data is accurate and legible. It may reduce risk of data replication as the data is centralized. Due to the digital information being searchable, EMRs may be more effective when extracting medical data for the examination of possible trends and long term changes in a patient. Population-based studies of medical records may also be facilitated by the widespread adoption of EHRs and EMRs.

Health Level-7 or HL7 refers to a set of international standards for transfer of clinical and administrative data between software applications used by various healthcare providers. These standards focus on the application layer, which is layer 7 in the OSI model. Hospitals and other healthcare provider organizations may have many different computer systems used for everything from billing records to patient tracking. Ideally, all of these systems may communicate with each other when they receive new information or when they wish to retrieve information, but adoption of such approaches is not widespread. These data standards are meant to allow healthcare organizations to easily share clinical information. This ability to exchange information may help to minimize variability in medical care and the tendency for medical care to be geographically isolated.

In various systems, connections between a PACS, Electronic Medical Record (EMR), Hospital Information System (HIS), Radiology Information System (RIS), or report repository are provided. In this way, records and reports form the EMR may be ingested for analysis. For example, in addition to ingesting and storing HL7 orders and results messages, ADT messages may be used, or an EMR, RIS, or report repository may be queried directly via product specific mechanisms. Such mechanisms include Fast Health Interoperability Resources (FHIR) for relevant clinical information. Clinical data may also be obtained via receipt of various HL7 CDA documents such as a Continuity of Care Document (CCD). Various additional proprietary or site-customized query methods may also be employed in addition to the standard methods.

Figure 3:
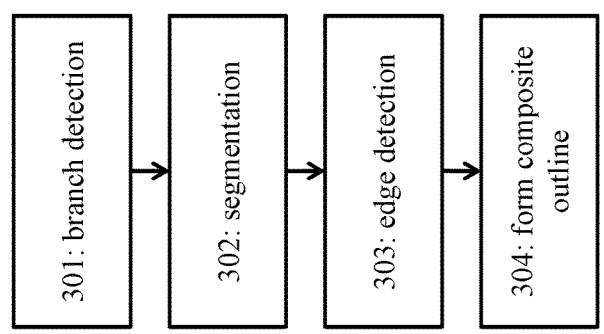
FIG. 3 illustrates a method of vessel segmentation according to embodiments of the present disclosure.

Referring now to FIG. 3, a method of vessel segmentation is illustrated according to embodiments of the present disclosure. At 301, a branch detection algorithm is applied to a medical image to determine a plurality of branches of a blood vessel appearing in the medical image. At 302, a plurality of segments of the blood vessel appearing in the medical image is determined. Each of the plurality of segments is bounded by one of the plurality of branches. At 303, an edge detection algorithm is applied piecewise to each of the plurality of segments. At 304, a composite blood vessel outline is formed from the piecewise edge detection.

Figure 4:
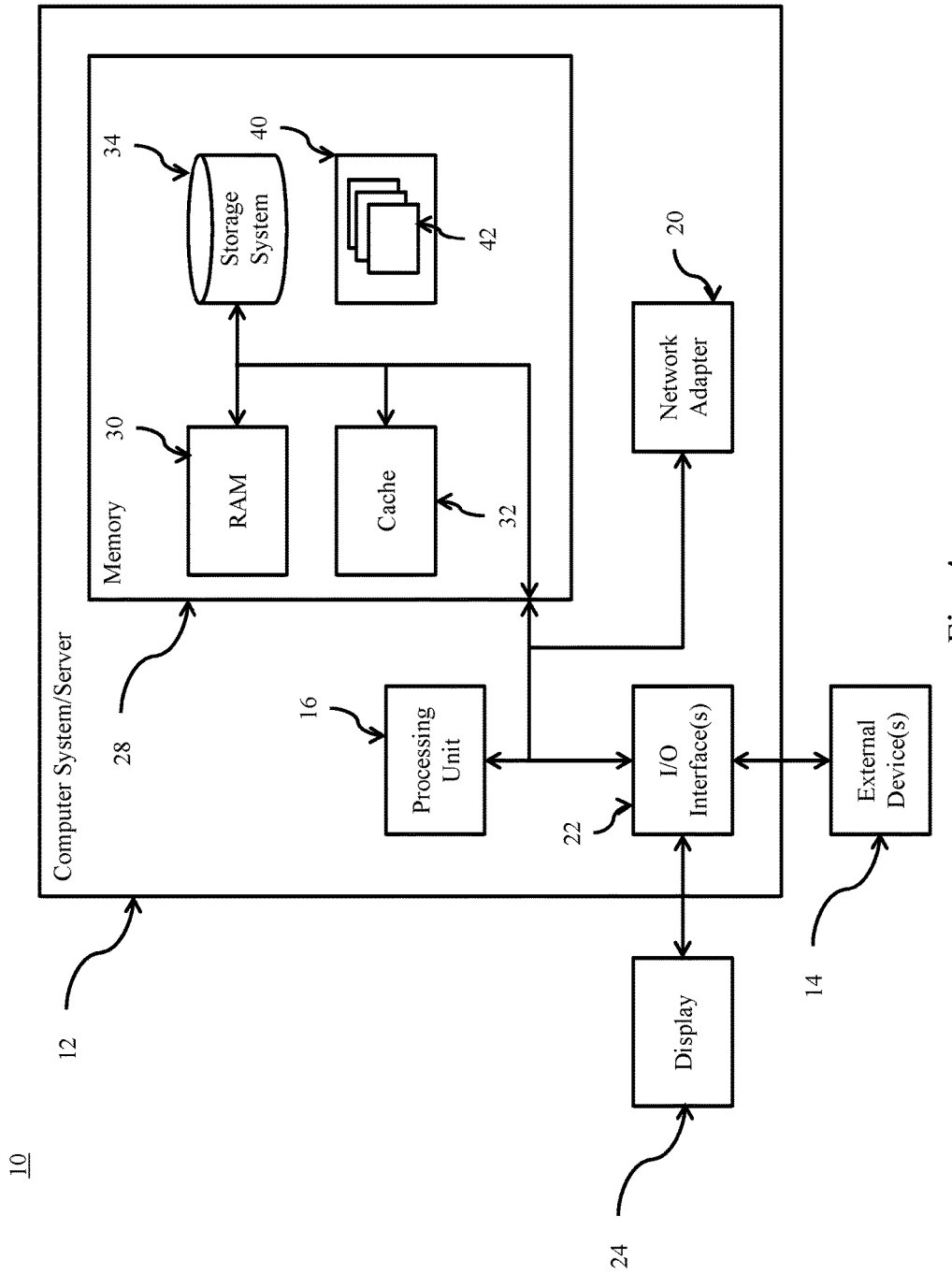
FIG. 4 depicts a computing node according to an embodiment of the present invention.

Referring now to FIG. 4, a schematic of an example of a computing node is shown. Computing node 10 is only one example of a suitable computing node and is not intended to suggest any limitation as to the scope of use or functionality of embodiments of the invention described herein. Regardless, computing node 10 is capable of being implemented and/or performing any of the functionality set forth hereinabove.

In computing node 10 there is a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 4, computer system/server 12 in computing node 10 is shown in the form of a general-purpose computing device. The components of computer system/ server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, external disk drive arrays, RAID systems, tape drives, and data archival storage systems, etc.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method comprising:
applying a branch detection algorithm to a medical image to determine a plurality of branches of a blood vessel appearing in the medical image;
determining a plurality of segments of the blood vessel appearing in the medical image, each of the plurality of segments being bounded by one of the plurality of branches;
applying an edge detection algorithm piecewise to each of the plurality of segments;
forming a composite blood vessel outline from the piecewise edge detection.

2. The method of claim 1, further comprising:
adding annotations to the medical image corresponding to each of the plurality of segments.

3. The method of claim 1, further comprising:
measuring a width of the blood vessel within each of the plurality of segments.

4. The method of claim 1, further comprising:
determining the relative dominance of each of the plurality of segments.

5. The method of claim 3, further comprising:
determining the presence of stenosis based on the width.

6. The method of claim 1, wherein the medical image originates from a modality, the modality being x-ray angiography, X-ray plain film, ultrasound, magnetic resonance, nuclear medicine imaging, positron emission tomography, or computed tomography.

7. The method of claim 1, further comprising determining a centerline of the blood vessel from the composite blood vessel outline.

8. The method of claim 1, further comprising:
registering at least one of the plurality of segments in an anatomical atlas.

9. The method of claim 8, further comprising:
exporting the plurality of segments to a reporting system or a hemodynamic system.

10. The method of claim 3, further comprising:
determining a stenosis value based on the width of the blood vessel within each of the plurality of segments.

11. The method of claim 9, wherein exporting the plurality of segments comprises applying syntax scoring.

12. The method of claim 9 where the completed automatic segmentation, labelling and stenosis values are displayed in the viewing and reporting systems as a coronary tree diagram.

13. A method comprising:
displaying to a user a first plurality of medical images;
receiving from a user indications of edges of blood vessels in the first plurality of medical images;
training a neural network based on the indications of edges of blood vessels;
applying the neural network to a second plurality of medical images;
receiving from the neural network indications of edges of blood vessels in the second plurality of medical images;
displaying to a user the indications of edges of blood vessels in the second plurality of medical images;

receiving from the user an acceptance or rejection of each of the indications of edges of blood vessels in the second plurality of medical images;

further training the neural network based on those indications of edges of blood vessels in the second plurality of medical images accepted by the user.

14. A computer program product for vessel segmentation, the computer program product comprising a non-transitory computer readable storage medium having program instructions embodied therewith, the program instructions executable by a processor to cause the processor to perform a method comprising:

applying a branch detection algorithm to a medical image to determine a plurality of branches of a blood vessel appearing in the medical image;

determining a plurality of segments of the blood vessel appearing in the medical image, each of the plurality of segments being bounded by one of the plurality of branches;

applying an edge detection algorithm piecewise to each of the plurality of segments;

forming a composite blood vessel outline from the piecewise edge detection.

15. The computer program product of claim 14, further comprising:

adding annotations to the medical image corresponding to each of the plurality of segments.

16. The computer program product of claim 14, further comprising:

measuring a width of the blood vessel within each of the plurality of segments.

17. The computer program product of claim 16, further comprising:

determining the presence of stenosis based on the width.

18. The computer program product of claim 14, further comprising:

determining the relative dominance of each of the plurality of segments.

19. The computer program product of claim 14, wherein the medical image originates from a modality, the modality being x-ray angiography, X-ray plain film, ultrasound, magnetic resonance, nuclear medicine imaging, positron emission tomography, or computed tomography.

20. The computer program product of claim 14, further comprising determining a centerline of the blood vessel from the composite blood vessel outline.

* * * * *